United States Patent [19]
Allen et al.

[11] Patent Number: 5,412,085
[45] Date of Patent: May 2, 1995

[54] POLLEN-SPECIFIC PROMOTER FROM MAIZE

[75] Inventors: Rebecca L. Allen; David M. Lonsdale, both of Norwich, United Kingdom

[73] Assignee: Pioneer Hi-Bred International Inc., Des Moines, Iowa

[21] Appl. No.: 149,695

[22] Filed: Nov. 9, 1993

Related U.S. Application Data

[63] Continuation of Ser. No. 911,532, Jul. 9, 1992, abandoned.

[51] Int. Cl.⁶ ...................... C07H 17/00; C12N 15/00
[52] U.S. Cl. ................................ 536/24.1; 435/172.3; 435/320.1
[58] Field of Search ........................ 800/205, DIG. 56; 435/172.3, 320.1; 935/41, 6, 67; 536/24.1

[56] References Cited

U.S. PATENT DOCUMENTS

| | | | |
|---|---|---|---|
| 4,394,443 | 7/1983 | Weissman et al. | 435/6 |
| 4,801,540 | 1/1989 | Hiatt et al. | 435/172.3 |
| 5,086,169 | 2/1992 | Mascarenhas | 536/27 |

OTHER PUBLICATIONS

Guerrero et al. (1990) Mol Gen Genetics 224: 161–168.
Pressey et al. (1989) Plant Science 59: 57–62.
Brown et al. (1990) The Plant Cell 2: 263–274.
Twell, D., et al. "Transient Expression of Chimeric Genes Delivered Into Pollen by Microprojectile Bombardment", Plant Physiol. 91 1270–1274, 1989.
Twell, D., et al. "Promoter Analysis of Genes that are Coordinately Expressed During Pollen Development Reveals Pollen-Specific Enhancer Sequences and Shared Regulatory Elements", Genes and Development 5:496–507, 1991.
Mascarenhas, et al. "Messenger RNAs in Corn Pollen and Protein Synthesis During Germination and Pollen Tube Growth", Theor. and Applied Genet. 68:323–326, 1984.
Hanson, et al. "Characterization of a Pollen-Specific DNA Clone from *Zea mays* and Its Expression", The Plant Cell 1:173–179, 1989.
Rogers, et al. "Pollen-Specific cDNA Clones from *Zea mays*", Biochimica et Biophysica Acta 1089, 411–413, 1991 Jul. 23.

*Primary Examiner*—David T. Fox
*Assistant Examiner*—Elizabeth F. McElwain
*Attorney, Agent, or Firm*—Foley & Lardner

[57] ABSTRACT

The present invention is related to isolated purified DNA sequences isolated from maize which can act as pollen-specific promoters and which play a role in the expression of genes in pollen. The present invention also relates to a method for conferring pollen-specificity on genes not normally expressed in pollen.

10 Claims, 17 Drawing Sheets

1 2 3 4 5 6 7 8 9

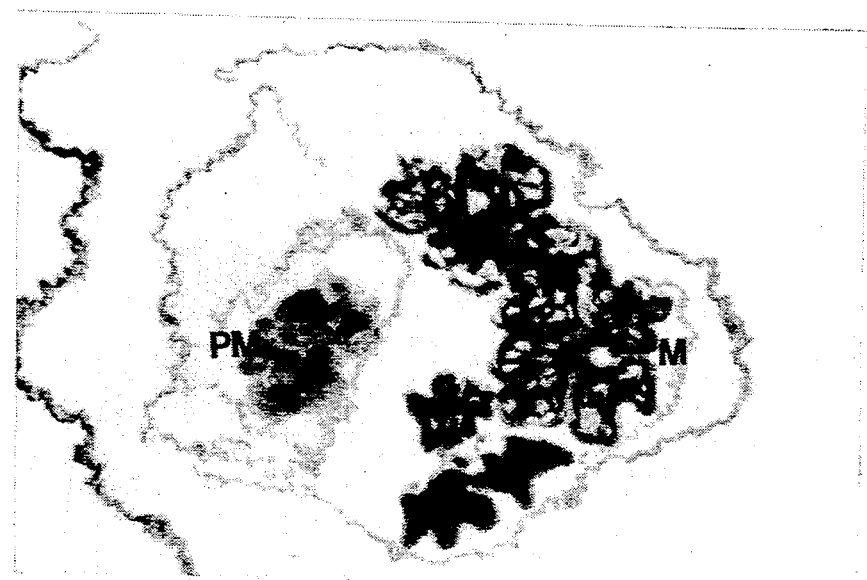
FIGURE 2A(1)

FIGURE 2A(2)
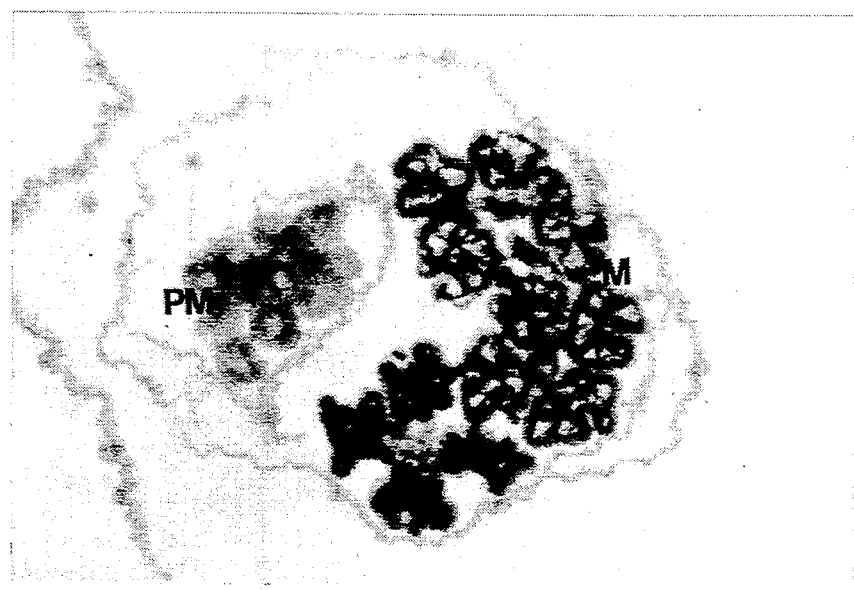

FIGURE 2B(1)
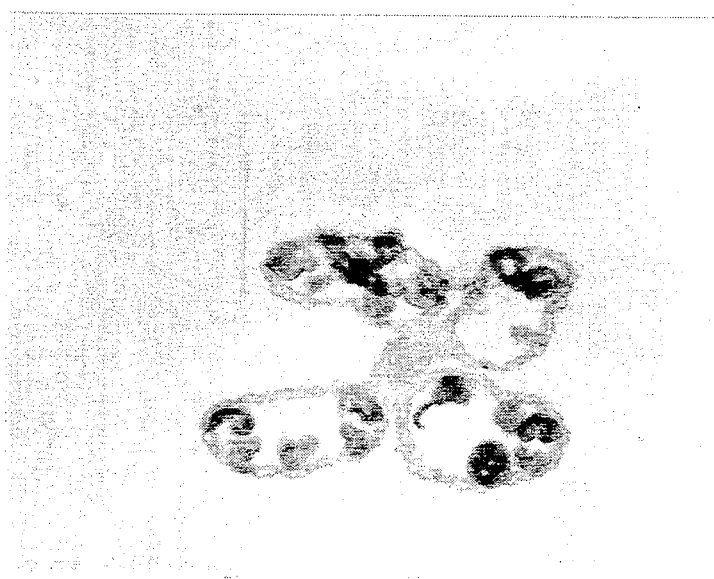

FIGURE 2B(2)
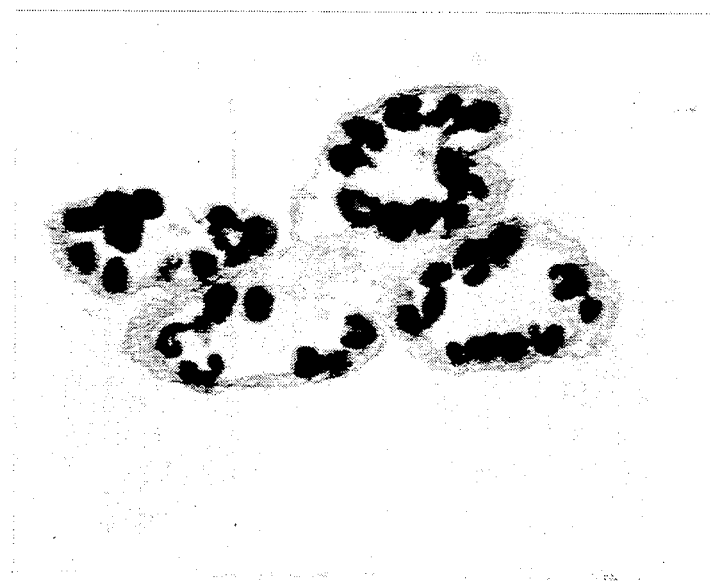

FIGURE 2C(1)

FIGURE 2C(2)
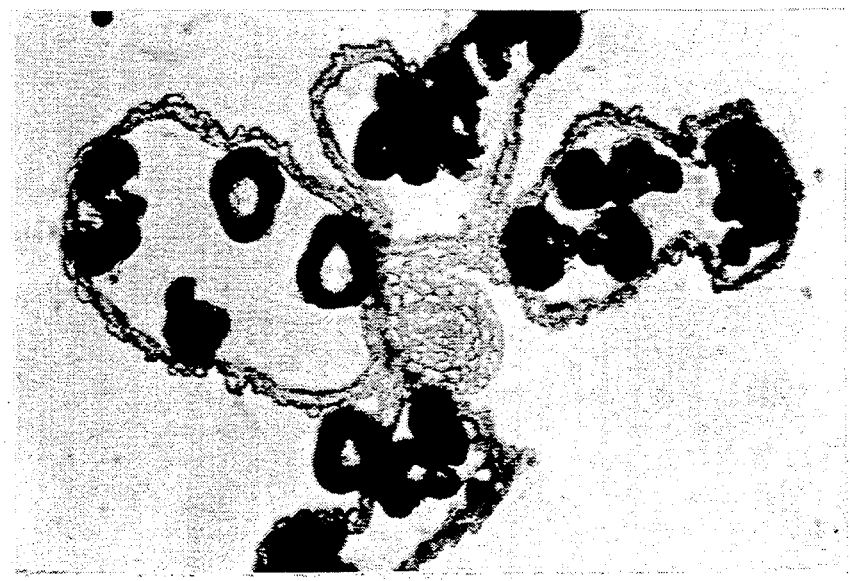

FIGURE 3a

```
GTCGACCGTT GCACTGTTAG CCGTTGCTCC GCTGGTGCAC CGGATAGTTC GGTGGCACAC  -2623
GGACAATCTG GTGAATTATA GTGGAGCAAC GCCTGAGAAA CCCGAAGTGG CGAGTTTGGA  -2563
GTTGTACGGT CCTGGTGCAC CGGACACTGT CTGGTGGCAT ACCAGACAGT CCGGTGTGCC  -2503
AGATCAGGGC ACCCTTCGGT TCCTTTGCTC CTTTGCTTTT GAACCCTAAC TTTGATCGTT  -2443
TATTGGTTTG TGTTGAACCT TTATGCACCT GTGGAATATA TAATCTAGAA CAAACTAGTT  -2383
AGTCCAATCA TTTGTGTTGG GCATTCAACC ACCAAAATTA TTTATAGGAA AAGGTTAAAC  -2323
CTTATTTCCC TTTCAATCTC CCCCTTTTTG GTGATTGATG CCAACACAAA CCAAAGAAAA  -2263
TATATAAGTG CAGAATTGAA CTAGTTTGCA TAAGGTAAGT GCATAGGTTA CTTAGAATTA  -2203
AATCAATTTA TACTTTTACT TGATATGCAT GGTTGCTTTC TTTTATTTTA ACATTTGGA   -2143
CCACATTTGC ACCACTTGTT TTGTTTTTTG CAAATCTTTT TGGAAATTCT TTTTCAAAGT  -2083
CTTTTGCAAA TAGTCAAAGG TATATGAATA AGATTGTAAG AAGCATTTTC AAGATTTGAA  -2023
ATTTCTCCCC CTGTTTCAAA TGCTTTTCCT TTGACTAAAC AAAACTCCCC CTGAATAAAA  -1963
TTCTCCTCTT AGCTTTCAAG AGGGTTTTAA ATAGATATCA TTTGAAATA TATTAGATG   -1903
CTAATTTGA AAATATACCA ATTGAAAATC AACATACCAA TTTGAAATTA AACATACCAA  -1843
TTTAAAAAAT TTCAAAAAGT GGTGGTGCGG TCCTTTTGCT TTGGGCTTAA TATTTCTCCC  -1783
CCTTTGGCAT TAACGGCCAA AAAACGGAGA CTTTGTGAGC CATTTATACT TTCTCCCCAT  -1723
TGGTAAATGA AATATGAGTG AAAGATTATA CCAAATTTGG ACAGTGATGC GGAGTGACGG  -1663
CGAAGGATAA ACGATACCGT TAGAGTGGAG TGGAAGCCTT GTCTTCGCCG AAGACTCCAT  -1603
```

FIGURE 3b

```
TTCCCTTTCA ATCTACGACT TAGCATAGAA ATACACTTGA AAACACATTA GTCGTAGCCA  -1543
CGAAAGAGAT ATGATCAAAG GTATACAAAT GAGCTATGTG TGTAATGTTT CAATCAAAGT  -1483
TTCGAGAATC AAGAATATTT AGCTCATTCC TAAGTTTGCT AAAGGTTTTA TCATCTAATG  -1423
GTTTGGTAAA GATATCGACT AATTGTTCTT TGGTGCTAAC ATAAGCAATC TCGATATCAC  -1363
CCCTTTGTTG GTGATCCCTC AAAAAGTGAT ACCGAATGTC TATGTGCTTA GTGCGGCTGT  -1303
GTTCAACGGG ATTATCCGCC ATGCAGATAG CACTCTCTCA TTGTCACATA GGAGAGGGAC  -1243
TTTGCTCAAT TTGTAGCCAT AGTCCCTAAG GTTTTGCCTC ATCCAAAGTA ATTGCACACA  -1183
ACAATGTCCT GCGGCAATAT ACTTGGCTTC GGCGGTAGAA AGAGCTATTG AGTTTGTTT   -1123
CTTTGAAGTC CAAGACACCA GGGATCTCCC TAGAAACTGA CAAGTCCCTG ATGTGCTCTT  -1063
CCTATCAATT TTACACCCTG CCCAATCGGC ATCTGAATAT CCTATTAAAT CAAAGGTGGA  -1003
TCCCTTGGGG TACCAAATTT AAGGAGTGTA AACTAAATAT CTCATGATTC TTTTCACGGC   -943
CCTAAGGTGA ACTTCCTTAG GATCGGCTTG GAATCTTGCA CACATGCATA TAGAAAGCAT   -883
ACTATCTGGT CGAGATGCAC ATAAATAGAG TAAAGATCCT ATCATCGACC GGTATACCTT   -823
TTGGTCTACG CCGTGTCGAG GTCGAGATGC CCATTAGTTC CCATGGGTGT              -763
CCTGATGGGC TTGGCATCCT TCATTCCAAA CTTGTTGAGT ATGTCTTGAA TGTACTTTGT   -703
TTGGCTGATG AAGGTGCCAT CTTGGAGTTG CTTGACTTGA AATCCTAGAA AATATTTCAA   -643
CTTCCCCATC ATAGACATCT CGAATTTCGG AATCATGATC CTACTAAACT CTTCACAAGT   -583
AGATTTGTTA GTAGACCCAA ATATAATATC ATCAAACATAA ATTTGGCATA CAAACAAAAC  -523
```

FIGURE 3c

```
TTTTGAAATG GTTTTAGTAA AGAGAGTAGG ATCGGCTTTA CTGACTCTGA AGCCATTAGT  -463
GATAAGAAAA TCTCTTAGGC ATTCATACCA TGCTGTTGGG GCTTGCTTGA GCCCATAAAG  -403
CGCCTTTGAG AGTTTATAAA CATGGTTAGG GTACTCACTA TCTTCAAAGC CGAGAGGTTG  -343
CTCAACATAG ACCTATTCAC CCCATTTGAT CACTTTTTTG GTCCCTTCAGG ATCTAATAGT  -283
TATGTATAAT TTAGAGTCTC TTGTTTAATG GCCAGATATT TCTAATTAAT CTAAGAATTT  -223
ATGATATTTT TTAATTTTTT ATCATGTCTG ATGAGAATTA ACATAAAGGC TCAATTGGGT  -163
CCTGAATTAA TAATAGAGTG AAAATTAATC CAGAGGCTCT ATTAGAACCT TCAATTAGTA  -103
ATACCAAGAT ATATATAAGA TAGTAGAGTA TAGTTTAAAT GTTGGCATTG TTCATTCTTT  -43
CTTTTGTTAT TTAATTTATG CTTTCCACGG TGGTTAGTGG TTACTTCTGA AGGGTCCAAA
TAATGCATGA AGAGTTTGAG GACAAGAAGT CTGCCCTAAA AATAGCGATG CAAAGGCATG
GTGTCCAAGC CATACACATA GCGCACTAAT TTTATCAGCA GAACAATGGT ATTTATAGGT
CCTAGTGCCC AGGCAACAAG AGACACGAAT AAAGCATCGA TCACGACAAG ATG
```

```
Tobacco  -148  AACTCTTAATAGTAAAAACAAAG -126
                |  |||||  ||   ||||||
Maize    -117  AACCTTGATAAATTAGTAATACCAAG -95
```

FIGURE 6

|  | TGTGGTT | PB CORE MOTIF |
|---|---|---|
| -14 | gGTGGTT | -8 |
| -1008 | gGTGGaT | -1002 |
| -1545 | cGTGGcT | -1547 |
| -1822 | gGTGGTg | -1816 |
| -1825 | aGTGGTg | -1819 |
| -2127 | aGTGGTg | -2133 |
| -2350 | gGTGGTT | -2356 |

|  | GAAT/ATTGTGA | LAT 56/59 BOX |
|---|---|---|
| -304 | aAAAaaGTGA | -313 |
| -359 | aAgATaGTGA | -368 |
| -470 | ccATTaGTGA | -461 |
| -590 | ctAcTTGTGA | -581 |
| -1343 | cAAAaaGTGA | -1334 |
| -1754 | GAcTTTGTGA | -1745 |

FIGURE 8

5' DELETIONS OF p47.427

| | | |
|---|---|---|
| -2687bp ──────── | ▨▨GUS▨▨nos-ter | p47.427 |
| -1579bp ─────── | ▨▨GUS▨▨nos-ter | D10.2 |
| -595bp ──── | ▨▨GUS▨▨nos-ter | D16.4 |
| -464bp ── | ▨▨GUS▨▨nos-ter | D16.6 |
| -377bp ── | ▨▨GUS▨▨nos-ter | D18.5 |
| -347bp ── | ▨▨GUS▨▨nos-ter | D17.2 |
| -80bp | ▨▨GUS▨▨nos-ter | D17.12 |

FIGURE 10

| Plasmid | Tobacco Pollen | Tobacco Leaf | Maize Leaf | Maize coleoptyle | Maize Cob | Maize Root |
|---|---|---|---|---|---|---|
| p47.427 | + | . | . | . | . | . |
| p47.430 | + | . | . | . | . | . |
| D10.2 | ++ | . | . | NT | . | . |
| D16.4 | ++ | . | . | . | . | . |
| D16.6 | ++ | . | . | . | . | . |
| D18.5 | ++ | . | . | . | . | . |
| D17.2 | + | . | . | . | . | . |
| D17.12 | + | . | . | . | . | . |
| CaMVADH::GUS | | ++ | + | + | + | + |

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2873 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Zea mays
        ( B ) STRAIN: Line W22
        ( F ) TISSUE TYPE: Pollen ( x i ) SEQUENCE DESCRIPTION: SEQ ID NO:1:

```
GTCGACCGTT  GCACTGTTAG  CCGTTGCTCC  GCTGGTGCAC  CGGATAGTTC  GGTGGCACAC      60

GGACAATCTG  GTGAATTATA  GTGGAGCAAC  GCCTGAGAAA  CCCGAAGTGG  CGAGTTTGGA     120

GTTGTACGGT  CCTGGTGCAC  CGGACACTGT  CTGGTGGCAT  ACCAGACAGT  CCGGTGTGCC     180

AGATCAGGGC  ACCCTTCGGT  TCCTTTGCTC  CTTTGCTTTT  GAACCCTAAC  TTTGATCGTT     240

TATTGGTTTG  TGTTGAACCT  TTATGCACCT  GTGGAATATA  TAATCTAGAA  CAAACTAGTT     300

AGTCCAATCA  TTTGTGTTGG  GCATTCAACC  ACCAAAATTA  TTTATAGGAA  AAGGTTAAAC     360
```

| | | | | | | |
|---|---|---|---|---|---|---|
| CTTATTTCCC | TTTCAATCTC | CCCCTTTTTG | GTGATTGATG | CCAACACAAA | CCAAAGAAAA | 420 |
| TATATAAGTG | CAGAATTGAA | CTAGTTTGCA | TAAGGTAAGT | GCATAGGTTA | CTTAGAATTA | 480 |
| AATCAATTTA | TACTTTTACT | TGATATGCAT | GGTTGCTTTC | TTTTATTTTA | ACATTTGGA | 540 |
| CCACATTTGC | ACCACTTGTT | TTGTTTTTTG | CAAATCTTTT | TGGAAATTCT | TTTCAAAGT | 600 |
| CTTTTGCAAA | TAGTCAAAGG | TATATGAATA | AGATTGTAAG | AAGCATTTTC | AAGATTTGAA | 660 |
| ATTTCTCCCC | CTGTTTCAAA | TGCTTTTCCT | TTGACTAAAC | AAAACTCCCC | CTGAATAAAA | 720 |
| TTCTCCTCTT | AGCTTTCAAG | AGGGTTTTAA | ATAGATATCA | ATTGGAAATA | TATTTAGATG | 780 |
| CTAATTTTGA | AAATATACCA | ATTGAAAATC | AACATACCAA | TTTGAAATTA | AACATACCAA | 840 |
| TTTAAAAAAT | TCAAAAAGT | GGTGGTGCGG | TCCTTTTGCT | TTGGGCTTAA | TATTTCTCCC | 900 |
| CCTTTGGCAT | TAACGGCCAA | AAAACGGAGA | CTTTGTGAGC | CATTTATACT | TTCTCCCCAT | 960 |
| TGGTAAATGA | AATATGAGTG | AAAGATTATA | CCAAATTTGG | ACAGTGATGC | GGAGTGACGG | 1020 |
| CGAAGGATAA | ACGATACCGT | TAGAGTGGAG | TGGAAGCCTT | GTCTTCGCCG | AAGACTCCAT | 1080 |
| TTCCCTTTCA | ATCTACGACT | TAGCATAGAA | ATACACTTGA | AAACACATTA | GTCGTAGCCA | 1140 |
| GGAAAGAGAT | ATGATCAAAG | GTATACAAAT | GAGCTATGTG | TGTAATGTTT | CAATCAAAGT | 1200 |
| TTCGAGAATC | AAGAATATTT | AGCTCATTCC | TAAGTTTGCT | AAAGGTTTTA | TCATCTAATG | 1260 |
| GTTTGGTAAA | GATATCGACT | AATTGTTCTT | TGGTGCTAAC | ATAAGCAATC | TCGATATCAC | 1320 |
| CCCTTTGTTG | GTGATCCCTC | AAAAAGTGAT | ACCGAATGTC | TATGTGCTTA | GTGCGGCTGT | 1380 |
| GTTCAACGGG | ATTATCCGCC | ATGCAGATAG | CACTCTCTCA | TTGTCACATA | GGAGAGGGAC | 1440 |
| TTTGCTCAAT | TTGTAGCCAT | AGTCCCTAAG | GTTTTGCCTC | ATCCAAAGTA | ATTGCACACA | 1500 |
| ACAATGTCCT | GCGGCAATAT | ACTTGGCTTC | GGCGGTAGAA | AGAGCTATTG | AGTTTGTTT | 1560 |
| CTTTGAAGTC | CAAGACACCA | GGGATCTCCC | TAGAAACTGA | CAAGTCCTG | ATGTGCTCTT | 1620 |
| CCTATCAATT | TTACACCCTG | CCCAATCGGC | ATCTGAATAT | CCTATTAAAT | CAAAGGTGGA | 1680 |
| TCCCTTGGGG | TACCAAATTT | AAGGAGTGTA | AACTAAATAT | CTCATGATTC | TTTTCACGGC | 1740 |
| CCTAAGGTGA | ACTTCCTTAG | GATCGGCTTG | GAATCTTGCA | CACATGCATA | TAGAAAGCAT | 1800 |
| ACTATCTGGT | CGAGATGCAC | ATAAATAGAG | TAAAGATCCT | ATCATCGACC | GGTATACCTT | 1860 |
| TTGGTCTACG | GATTTACCTC | CCGTGTCGAG | GTCGAGATGC | CCATTAGTTC | CCATGGGTGT | 1920 |
| CCTGATGGGC | TTGGCATCCT | TCATTCCAAA | CTTGTTGAGT | ATGTCTTGAA | TGTACTTTGT | 1980 |
| TTGGCTGATG | AAGGTGCCAT | CTTGGAGTTG | CTTGACTTGA | AATCCTAGAA | AATATTTCAA | 2040 |
| CTTCCCCATC | ATAGACATCT | CGAATTTCGG | AATCATGATC | CTACTAAACT | CTTCACAAGT | 2100 |
| AGATTTGTTA | GTAGACCCAA | ATATAATATC | ATCAACATAA | ATTTGGCATA | CAAACAAAAC | 2160 |
| TTTTGAAATG | GTTTTAGTAA | AGAGAGTAGG | ATCGGCTTTA | CTGACTCTGA | AGCCATTAGT | 2220 |
| GATAAGAAAA | TCTCTTAGGC | ATTCATACCA | TGCTGTTGGG | GCTTGCTTGA | GCCCATAAAG | 2280 |
| CGCCTTTGAG | AGTTTATAAA | CATGGTTAGG | GTACTCACTA | TCTTCAAAGC | CGAGAGGTTG | 2340 |
| CTCAACATAG | ACCTATTCAC | CCCATTTGAT | CACTTTTTG | GTCCTTCAGG | ATCTAATAGT | 2400 |
| TATGTATAAT | TTAGAGTCTC | TTGTTTAATG | GCCAGATATT | TCTAATTAAT | CTAAGAATTT | 2460 |
| ATGATATTTT | TTAATTTTTT | ATCATGTCTG | ATGAGAATTA | ACATAAAGGC | TCAATTGGGT | 2520 |
| CCTGAATTAA | TAATAGAGTG | AAAATTAATC | CAGAGGCTCT | ATTAGAACCT | TCAATTAGTA | 2580 |
| ATACCAAGAT | ATATATAAGA | TAGTAGAGTA | TAGTTTAAAT | GTTGGCATTG | TTCATTCTTT | 2640 |
| CTTTTGTTAT | TTAATTTATG | CTTTCCACGG | TGGTTAGTGG | TTACTTCTGA | AGGGTCCAAA | 2700 |
| TAATGCATGA | AGAGTTTGAG | GACAAGAAGT | CTGCCCTAAA | AATAGCGATG | CAAAGGCATG | 2760 |
| GTGTCCAAGC | CATACATATA | GCGCACTAAT | TTATCAGCA | GAACAATGGT | ATTTATAGGT | 2820 |

CCTAGTGCCC AGGCAACAAG AGACACGAAT AAAGCATCGA TCACGACAAG ATG 2873

( 2 ) INFORMATION FOR SEQ ID NO:2:

( i ) SEQUENCE CHARACTERISTICS:
  ( A ) LENGTH: 80 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Zea mays
  ( B ) STRAIN: Line W22

( x i ) SEQUENCE DESCRIPTION: SEQ ID NO:2:

ATCAGCAGAA CAATGGTATT TATAGGTCCT AGTGCCCAGG CAACAAGAGA CACGAATAAA 60

GCATCGATCA CGACAAGATG 80

( 2 ) INFORMATION FOR SEQ ID NO:3:

( i ) SEQUENCE CHARACTERISTICS:
  ( A ) LENGTH: 347 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Zea mays
  ( B ) STRAIN: Line W22

( x i ) SEQUENCE DESCRIPTION: SEQ ID NO:3:

TTAATAATAG AGTGAAAATT AATCCAGAGG CTCTATTAGA ACCTTCAATT AGTAATACCA 60

AGATATATAT AAGATAGTAG AGTATAGTTT AAATGTTGGC ATTGTTCATT CTTTCTTTTG 120

TTATTTAATT TATGCTTTCC ACGGTGGTTA GTGGTTACTT CTGAAGGGTC CAAATAATGC 180

ATGAAGAGTT TGAGGACAAG AAGTCTGCCC TAAAATAGC GATGCAAAGG CATGGTGTCC 240

AAGCCATACA TATAGCGCAC TAATTTTATC AGCAGAACAA TGGTATTTAT AGGTCCTAGT 300

GCCCAGGCAA CAAGAGACAC GAATAAAGCA TCGATCACGA CAAGATG 347

( 2 ) INFORMATION FOR SEQ ID NO:4:

( i ) SEQUENCE CHARACTERISTICS:
  ( A ) LENGTH: 377 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Zea mays
  ( B ) STRAIN: Line W22

( x i ) SEQUENCE DESCRIPTION: SEQ ID NO:4:

| ATTAACATAA | AGGCTCAATT | GGGTCCTGAA | TTAATAATAG | AGTGAAAATT | AATCCAGAGG | 60 |
|---|---|---|---|---|---|---|
| CTCTATTAGA | ACCTTCAATT | AGTAATACCA | AGATATATAT | AAGATAGTAG | AGTATAGTTT | 120 |
| AAATGTTGGC | ATTGTTCATT | CTTTCTTTTG | TTATTTAATT | TATGCTTTCC | ACGGTGGTTA | 180 |
| GTGGTTACTT | CTGAAGGGTC | CAAATAATGC | ATGAAGAGTT | TGAGGACAAG | AAGTCTGCCC | 240 |
| TAAAAATAGC | GATGCAAAGG | CATGGTGTCC | AAGCCATACA | TATAGCGCAC | TAATTTTATC | 300 |
| AGCAGAACAA | TGGTATTTAT | AGGTCCTAGT | GCCCAGGCAA | CAAGAGACAC | GAATAAAGCA | 360 |
| TCGATCACGA | CAAGATG | | | | | 377 |

(2) INFORMATION FOR SEQ ID NO:5:

(i) SEQUENCE CHARACTERISTICS:
        (A) LENGTH: 464 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Zea mays
        (B) STRAIN: Line W22

(xi) SEQUENCE DESCRIPTION: SEQ ID NO:5:

| TTTAGAGTCT | CTTGTTTAAT | GGCCAGATAT | TTCTAATTAA | TCTAAGAATT | TATGATATTT | 60 |
|---|---|---|---|---|---|---|
| TTTAATTTTT | TATCATGTCT | GATGAGAATT | AACATAAAGG | CTCAATTGGG | TCCTGAATTA | 120 |
| ATAATAGAGT | GAAAATTAAT | CCAGAGGCTC | TATTAGAACC | TTCAATTAGT | AATACCAAGA | 180 |
| TATATATAAG | ATAGTAGAGT | ATAGTTTAAA | TGTTGGCATT | GTTCATTCTT | CTTTTGTTA | 240 |
| TTTAATTTAT | GCTTTCCACG | GTGGTTAGTG | GTTACTTCTG | AAGGGTCCAA | ATAATGCATG | 300 |
| AAGAGTTTGA | GGACAAGAAG | TCTGCCCTAA | AAATAGCGAT | GCAAAGGCAT | GGTGTCCAAG | 360 |
| CCATACATAT | AGCGCACTAA | TTTTATCAGC | AGAACAATGG | TATTTATAGG | TCCTAGTGCC | 420 |
| CAGGCAACAA | GAGACACGAA | TAAAGCATCG | ATCACGACAA | GATG | | 464 |

(2) INFORMATION FOR SEQ ID NO:6:

(i) SEQUENCE CHARACTERISTICS:
        (A) LENGTH: 595 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Zea mays
        (B) STRAIN: Line W22

(xi) SEQUENCE DESCRIPTION: SEQ ID NO:6:

| AGCGCCTTTG | AGAGTTTATA | AACATGGTTA | GGGTACTCAC | TATCTTCAAA | GCCGAGAGGT | 60 |
|---|---|---|---|---|---|---|
| TGCTCAACAT | AGACCTATTC | ACCCCATTTG | ATCACTTTTT | TGGTCCTTCA | GGATCTAATA | 120 |
| GTTATGTATA | ATTTAGAGTC | TCTTGTTTAA | TGGCCAGATA | TTTCTAATTA | ATCTAAGAAT | 180 |
| TTATGATATT | TTTTAATTTT | TTATCATGTC | TGATGAGAAT | TAACATAAAG | GCTCAATTGG | 240 |
| GTCCTGAATT | AATAATAGAG | TGAAAATTAA | TCCAGAGGCT | CTATTAGAAC | CTTCAATTAG | 300 |

| | | | | | |
|---|---|---|---|---|---|
| TAATACCAAG | ATATATATAA | GATAGTAGAG | TATAGTTTAA | ATGTTGGCAT | TGTTCATTCT | 360
| TTCTTTTGTT | ATTTAATTTA | TGCTTTCCAC | GGTGGTTAGT | GGTTACTTCT | GAAGGGTCCA | 420
| AATAATGCAT | GAAGAGTTTG | AGGACAAGAA | GTCTGCCCTA | AAAATAGCGA | TGCAAAGGCA | 480
| TGGTGTCCAA | GCCATACATA | TAGCGCACTA | ATTTATCAG | CAGAACAATG | GTATTTATAG | 540
| GTCCTAGTGC | CCAGGCAACA | AGAGACACGA | ATAAAGCATC | GATCACGACA | AGATG | 595

(2) INFORMATION FOR SEQ ID NO:7:

(i) SEQUENCE CHARACTERISTICS:
        (A) LENGTH: 1579 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: zea mays
        (B) STRAIN: Line W22

(xi) SEQUENCE DESCRIPTION: SEQ ID NO:7:

| | | | | | |
|---|---|---|---|---|---|
| GCTAACATAA | GCAATCTCGA | TATCACCCCT | TGTTGGTGA | TCCCTCAAAA | AGTGATACCG | 60
| AATGTCTATG | TGCTTACTGC | GGCTGTGTTC | AACGGGATTA | TCCGCCATGC | AGATAGCACT | 120
| CTCTCATGTT | CACATAGGAG | AGGGACTTTG | CTCAATTTGT | AGCCATAGTC | CCTAAGGTTT | 180
| TGCCTCATCC | AAAGTAATTG | CACACAACAA | TGTCCTGCGG | CAATATACTT | GGCTTCGGCG | 240
| GTAGAAAGAG | CTATTGAGTT | TTGTTTCTTT | GAAGTCCAAG | ACACCAGGGA | TCTCCCTAGA | 300
| AACTGACAAG | TCCCTGATGT | GCTCTTCCTA | TCAATTTTAC | ACCCTGCCCA | ATCGGCATCT | 360
| GAATATCCTA | TTAAATCAAA | GGTGGATCCC | TTGGGGTACC | AAATTTAAGG | AGTGTAAACT | 420
| AAATATCTCA | TGATTCTTTT | CACGGCCCTA | AGGTGAACTT | CCTTAGGATC | GGCTTGGAAT | 480
| CTTGCACACA | TGCATATAGA | AAGCATACTA | TCTGGTCGAG | ATGCACATAA | ATAGAGTAAA | 540
| GATCCTATCA | TCGACCGGTA | TACCTTTTGG | TCTACGGATT | TACCTCCCGT | GTCGAGGTCG | 600
| AGATGCCCAT | TAGTTCCCAT | GGGTGTCCTG | ATGGGCTTGG | CATCCTTCAT | TCCAAACTTG | 660
| TTGAGTATGT | CTTGAATGTA | CTTTGTTTGG | CTGATGAAGG | TGCCATCTTG | GAGTTGCTTG | 720
| ACTTGAAATC | CTAGAAAATA | TTTCAACTTC | CCCATCATAG | ACATCTCGAA | TTTCGGAATC | 780
| ATGATCCTAC | TAAACTCTTC | ACAAGTAGAT | TTGTTAGTAG | ACCCAAATAT | AATATCATCA | 840
| ACATAAATTT | GGCATACAAA | CAAAACTTTT | GAAATGGTTT | TAGTAAAGAG | AGTAGGATCG | 900
| GCTTTACTGA | CTCTGAAGCC | ATTAGTGATA | AGAAAATCTC | TTAGGCATTC | ATACCATGCT | 960
| GTTGGGGCTT | GCTTGAGCCC | ATAAAGCGCC | TTTGAGAGTT | TATAAACATG | GTTAGGGTAC | 1020
| TCACTATCTT | CAAAGCCGAG | AGGTTGCTCA | ACATAGACCT | ATTCACCCCA | TTTGATCACT | 1080
| TTTTTGGTCC | TTCAGGATCT | AATAGTTATG | TATAATTTAG | AGTCTCTTGT | TTAATGGCCA | 1140
| GATATTTCTA | ATTAATCTAA | GAATTTATGA | TATTTTTTAA | TTTTTATCA | TGTCTGATGA | 1200
| GAATTAACAT | AAAGGCTCAA | TTGGGTCCTG | AATTAATAAT | AGAGTGAAAA | TTAATCCAGA | 1260
| GGCTCTATTA | GAACCTTCAA | TTAGTAATAC | CAAGATATAT | ATAAGATAGT | AGAGTATAGT | 1320
| TTAAATGTTG | GCATTGTTCA | TTCTTTCTTT | TGTTATTTAA | TTTATGCTTT | CCACGGTGGT | 1380
| TAGTGGTTAC | TTCTGAAGGG | TCCAAATAAT | GCATGAAGAG | TTTGAGGACA | AGAAGTCTGC | 1440
| CCTAAAAATA | GCGATGCAAA | GGCATGGTGT | CCAAGCCATA | CATATAGCGC | ACTAATTTTA | 1500
| TCAGCAGAAC | AATGGTATTT | ATAGGTCCTA | GTGCCCAGGC | AACAAGAGAC | ACGAATAAAG | 1560

CATCGATCAC GACAAGATG                                                          1579

( 2 ) INFORMATION FOR SEQ ID NO:8:

( i ) SEQUENCE CHARACTERISTICS:
        ( A ) LENGTH: 2687 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Zea mays
        ( B ) STRAIN: Line W22

( x i ) SEQUENCE DESCRIPTION: SEQ ID NO:8:

```
GGGCACCCTT CGGTTCCTTT GCTCCTTTGC TTTTGAACCC TAACTTTGAT CGTTTATTGG    60
TTTGTGTTGA ACCTTTATGC ACCTGTGGAA TATATAATCT AGAACAAACT AGTTAGTCCA   120
ATCATTTGTG TTGGGCATTC AACCACCAAA ATTATTTATA GGAAAAGGTT AAACCTTATT   180
TCCCTTTCAA TCTCCCCCTT TTTGGTGATT GATGCCAACA CAAACCAAAG AAAATATATA   240
AGTGCAGAAT TGAACTAGTT TGCATAAGGT AAGTGCATAG GTTACTTAGA ATTAAATCAA   300
TTTATACTTT TACTTGATAT GCATGGTTGC TTTCTTTTAT TTTAACATTT TGGACCACAT   360
TTGCACCACT TGTTTTGTTT TTTGCAAATC TTTTTGGAAA TTCTTTTTCA AAGTCTTTTG   420
CAAATAGTCA AAGGTATATG AATAAGATTG TAAGAAGCAT TTTCAAGATT TGAAATTTCT   480
CCCCCTGTTT CAAATGCTTT TCCTTTGACT AAACAAAACT CCCCCTGAAT AAAATTCTCC   540
TCTTAGCTTT CAAGAGGGTT TTAAATAGAT ATCAATTGGA AATATATTTA GATGCTAATT   600
TTGAAAATAT ACCAATTGAA AATCAACATA CCAATTTGAA ATTAAACATA CCAATTTAAA   660
AAATTTCAAA AAGTGGTGGT GCGGTCCTTT TGCTTTGGGC TTAATATTTC TCCCCCTTTG   720
GCATTAACGG CCAAAAAACG GAGACTTTGT GAGCCATTTA TACTTCTCC  CCATTGGTAA   780
ATGAAATATG AGTGAAAGAT TATACCAAAT TTGGACAGTG ATGCGGAGTG ACGGCGAAGG   840
ATAAACGATA CCGTTAGAGT GGAGTGGAAG CCTTGTCTTC GCCGAAGACT CCATTTCCCT   900
TTCAATCTAC GACTTAGCAT AGAAATACAC TTGAAACAC  ATTAGTCGTA GCCAGGAAAG   960
AGATATGATC AAAGGTATAC AAATGAGCTA TGTGTGTAAT GTTTCAATCA AGTTTCGAG   1020
AATCAAGAAT ATTTAGCTCA TTCCTAAGTT TGCTAAAGGT TTTATCATCT AATGGTTTGG   1080
TAAAGATATC GACTAATTGT TCTTTGGTGC TAACATAAGC AATCTCGATA TCACCCCTTT   1140
GTTGGTGATC CCTCAAAAAG TGATACCGAA TGTCTATGTG CTTAGTGCGG CTGTGTTCAA   1200
CGGGATTATC CGCCATGCAG ATAGCACTCT CTCATTGTCA CATAGGAGAG GGACTTTGCT   1260
CAATTTGTAG CCATAGTCCC TAAGGTTTTG CCTCATCCAA AGTAATTGCA CACAACAATG   1320
TCCTGCGGCA ATATACTTGG CTTCGGCGGT AGAAAGAGCT ATTGAGTTTT GTTTCTTTGA   1380
AGTCCAAGAC ACCAGGGATC TCCCTAGAAA CTGACAAGTC CCTGATGTGC TCTTCCTATC   1440
AATTTTACAC CCTGCCCAAT CGGCATCTGA ATATCCTATT AAATCAAAGG TGGATCCCTT   1500
GGGGTACCAA ATTTAAGGAG TGTAAACTAA ATATCTCATG ATTCTTTTCA CGGCCCTAAG   1560
GTGAACTTCC TTAGGATCGG CTTGGAATCT TGCACACATG CATATAGAAA GCATACTATC   1620
TGGTCGAGAT GCACATAAAT AGAGTAAAGA TCCTATCATC GACCGGTATA CCTTTTGGTC   1680
TACGGATTTA CCTCCCGTGT CGAGGTCGAG ATGCCCATTA GTTCCCATGG GTGTCCTGAT   1740
```

-continued

| | | | | | | |
|---|---|---|---|---|---|---|
| GGGCTTGGCA | TCCTTCATTC | CAAACTTGTT | GAGTATGTCT | TGAATGTACT | TTGTTTGGCT | 1800 |
| GATGAAGGTG | CCATCTTGGA | GTTGCTTGAC | TTGAAATCCT | AGAAAATATT | TCAACTTCCC | 1860 |
| CATCATAGAC | ATCTCGAATT | TCGGAATCAT | GATCCTACTA | AACTCTTCAC | AAGTAGATTT | 1920 |
| GTTAGTAGAC | CCAAATATAA | TATCATCAAC | ATAAATTTGG | CATACAAACA | AAACTTTTGA | 1980 |
| AATGGTTTTA | GTAAAGAGAG | TAGGATCGGC | TTTACTGACT | CTGAAGCCAT | TAGTGATAAG | 2040 |
| AAAATCTCTT | AGGCATTCAT | ACCATGCTGT | TGGGGCTTGC | TTGAGCCCAT | AAAGCGCCTT | 2100 |
| TGAGAGTTTA | TAAACATGGT | TAGGGTACTC | ACTATCTTCA | AAGCCGAGAG | GTTGCTCAAC | 2160 |
| ATAGACCTAT | TCACCCCATT | TGATCACTTT | TTTGGTCCTT | CAGGATCTAA | TAGTTATGTA | 2220 |
| TAATTTAGAG | TCTCTTGTTT | AATGGCCAGA | TATTTCTAAT | TAATCTAAGA | ATTTATGATA | 2280 |
| TTTTTTAATT | TTTTATCATG | TCTGATGAGA | ATTAACATAA | AGGCTCAATT | GGGTCCTGAA | 2340 |
| TTAATAATAG | AGTGAAAATT | AATCCAGAGG | CTCTATTAGA | ACCTTCAATT | AGTAATACCA | 2400 |
| AGATATATAT | AAGATAGTAG | AGTATAGTTT | AAATGTTGGC | ATTGTTCATT | CTTTCTTTTG | 2460 |
| TTATTTAATT | TATGCTTTCC | ACGGTGGTTA | GTGGTTACTT | CTGAAGGGTC | CAAATAATGC | 2520 |
| ATGAAGAGTT | TGAGGACAAG | AAGTCTGCCC | TAAAATAGC | GATGCAAAGG | CATGGTGTCC | 2580 |
| AAGCCATACA | TATAGCGCAC | TAATTTTATC | AGCAGAACAA | TGGTATTTAT | AGGTCCTAGT | 2640 |
| GCCCAGGCAA | CAAGAGACAC | GAATAAAGCA | TCGATCACGA | CAAGATG | | 2687 |

POLLEN-SPECIFIC PROMOTER FROM MAIZE

This application is a continuation of application Ser. No. 07/911,532, filed Jul. 9, 1992, now abandoned.

FIELD OF THE INVENTION

The present invention is related to isolated, purified DNA sequences which can act as promoters in eukaryotic cells. More specifically, the present invention is related to isolated purified DNA sequences from maize which act as pollen-specific promoters and play a role in the expression of genes in pollen. The present invention is also directed to a method for conferring on a gene, which is not normally expressed in pollen, the ability to be expressed in a pollen-specific manner.

BACKGROUND OF THE INVENTION

Male gametogenesis in maize has been well characterized biochemically and cytologically, but our understanding of the molecular events controlling this key process in the angiosperm life cycle is at present minimal. The complex differentiation of a maize pollen mother cell into the highly specialized trinucleate pollen grain suggests that male gametogenesis involves the sequential production of many gene products. However, only a few genes involved in male gametogenesis in flowering plants have been isolated.

Evidence for the sequential expression of genes in the anther comes from the identification of two classes of transcripts expressed during male gametogenesis (Mascarenhas 1990); the "early" genes are expressed postmeiotically with their levels increasing before declining as the pollen grains mature. The "late" genes are switched on after microspore mitosis and increase to a maximum in mature pollen. It has been estimated (Willing et al. 1988) that around 20,000 genes are expressed in maize pollen and possibly up to 10% are pollen-specific (Stinson et al. 1987). The only reported pollen-specific genes cloned from maize are Zm13 (Hanson et al. 1989) and Zm58 (Mascarenhas 1990). The expression of these genes can first be detected following microspore mitosis and they increase to a maximum in mature pollen. Zmc13 shows homology in its predicted amino acid sequence to Kunitz trypsin inhibitor proteins and also to a tomato anther-expressed gene LAT52 (Hanson et al. 1989). Zm58 shows homology in its predicted amino acid sequence to pectate lyases (Mascarenhas 1990). It is suspected that the products of genes in this class have a role in pollen germination and/or pollen tube growth, whereas products of the "early" genes are more likely to be involved in microspore development.

Sequence comparisons and mutagenesis experiments have implicated certain DNA sequence motifs in the control of pollen expression of the LAT genes in tomato (Twell et al. 1991). Sequence comparisons alone have been used for the putative identification of a region involved in anther specific expression in petunia (van Tunen et al. 1989).

At present, little is known of possible cis-acting sequences in the maize genome that may be responsible for the tissue-specific expression of functions peculiar to pollen development. However, the maize clone, Zm13, does possess several regions of homology with the proposed pollen boxes identified in the tomato LAT genes.

Rogers et al. 1991 have described the isolation of a cDNA clone, 3C12 (incomplete at its 5' end), from maize which shows homology in its predicted amino acid sequence to polygalacturonases (PG) from both eucaryotic and procaryotic species, including a pollen-expressed PG from *Oenothera organensis* (Brown and Crouch 1990). Polygalacturonase has been detected in the pollen of maize and other monocotyledonous plant species (Pressey and Reger 1989). It is possible that the function of polygalacturonase in the pollen grain is in the growth of the pollen tube down the silk by hydrolyzing pectin and providing components which can be used as precursors of the pollen tube cell wall, or it may be involved in the degradation of cellular material within the silk to allow penetration of the tube. Allen and Lonsdale (submitted for publication) have also described the isolation, by use of the 5' end of the maize clone 3C12 as a probe, of 4 genomic PG clones. Analysis of the sequence of three of the PG genomic clones suggests that polygalacturonases are members of a multigene family (Allen and Lonsdale submitted for publication). The polygalacturonase gene isolated from tomato and involved in fruit-ripening (Grierson et al. 1986) is present in a single copy in the tomato genome. Brown and Crouch (1990) isolated at least six unique cDNA clones with homology to polygalacturonase from a pollen cDNA library of *Oenothera organensis*, suggesting that multiple PG genes are expressed in pollen of that species.

Of the 2,000 possible pollen-specific genes of maize, only two have been characterized. U.S. Pat. No. 5,086,169 ('169) discloses the nucleotide sequence of an isolated pollen-specific promoter called Zm13 from an unidentified gene expressed in corn. The pollen-specific promoter sequence consists of 1315 base pairs upstream from a region of DNA which hybridizes to mRNA found only in pollen. This is the same pollen-specific promoter described by Hanson et al. (1989).

It is an object of the present invention to isolate and characterize a DNA sequence which is capable of acting as a pollen-specific promoter. More particularly, it is an object of the invention to isolate and characterize a pollen-specific promoter region taken from a pollen-specific polygalacturonase gene.

SUMMARY OF THE INVENTION

The present invention relates to an isolated, purified DNA sequence from the promoter region of a pollen-specific gene of inbred corn line W22. The isolated purified DNA sequence consists essentially of the sequence set forth in FIGS. 3A–3C. The invention further relates to an isolated, purified DNA sequence corresponding to the pollen-specific promoter region of polygalacturonase. The invention still further relates to an isolated, purified DNA sequence from the promoter region of a pollen-specific gene of inbred corn line W22 as set forth in FIGS. 3A–3C, (SEQ ID NO: 1) the sequence selected from the group consisting of from:

a) about 1 to about 80 bases upstream from the 3' end of the promoter region (SEQ ID NO: 2);
b) about 1 to about 347 base-pairs upstream from the 3' end of the promoter region (SEQ ID NO: 3);
c) about 1 to about 377 base-pairs upstream from the 3' end of the promoter region (SEQ ID NO: 4);
d) about 1 to about 464 base-pairs of DNA upstream of the 3' end of the promoter region (SEQ ID NO: 5);
e) about 1 to about 595 base-pairs upstream from the 3' end of the promoter region (SEQ ID NO: 6);

f) about 1 to about 1579 base-pairs of DNA upstream from the 3' end of the promoter region (SEQ ID NO: 7); and g) about 1 to about 2687 base-pairs upstream from the 3' end of the promoter region (SEQ ID NO: 8).

The present invention also relates to a pollen-specific chimeric gene comprising a gene whose wild type promoter is replaced with a DNA sequence taken from the group consisting of from:

a) about 1 to about 80 bases upstream from the 3' end of the promoter region (SEQ ID NO: 2);

b) about 1 to about 347 base-pairs upstream from the 3' end of the promoter region (SEQ ID NO: 3);

c) about 1 to about 377 base-pairs upstream from the 3' end of the promoter region (SEQ ID NO: 4);

d) about 1 to about 464 base-pairs of DNA upstream of the 3' end of the promoter region (SEQ ID NO: 5);

e) about 1 to about 595 base-pairs upstream from the 3' end of the promoter region (SEQ ID NO: 6);

f) about 1 to about 1579 base-pairs of DNA upstream from the 3' end of the promoter region (SEQ ID NO: 7); and g) about 1 to about 2687 base-pairs upstream from the 3' end of the promoter region (SEQ ID NO: 8).

The present invention also relates to a pollen-specific chimeric gene further comprising a transfer vector.

Another aspect of the invention relates to a method for conferring pollen-specific expression on a gene, the method comprising:

a) replacing a wild type promoter region of a gene with a pollen-specific promoter region consisting essentially of the sequence set forth in FIG. 1, thereby creating a pollen-specific chimeric gene;

b) introducing the pollen-specific chimeric gene into a transfer vector;

c) introducing the transfer vector containing the pollen-specific chimeric gene into pollen which is capable of assimilating and expressing the chimeric gene; and d) testing for expression of the chimeric gene in the pollen.

The present invention also relates to the method described above wherein the pollen-specific promoter region for conferring pollen-specific expression on a gene is selected from a group consisting of from:

a) about 1 to about 80 bases upstream from the 3' end of the promoter region (SEQ ID NO: 2);

b) about 1 to about 347 base-pairs upstream from the 3' end of the promoter region (SEQ ID NO: 3);

c) about 1 to about 377 base-pairs upstream from the 3' end of the promoter region (SEQ ID NO: 4);

d) about 1 to about 464 base-pairs of DNA upstream of the 3' end of the promoter region (SEQ ID NO: 5);

e) about 1 to about 595 base-pair upstream from the 3' end of the promoter region (SEQ ID NO: 6);

f) about 1 to about 1579 base-pairs of DNA upstream from the 3' end of the promoter region (SEQ ID NO: 7); and g) about 1 to about 2687 base-pairs upstream from the 3' end of the promoter region (SEQ ID NO: 8).

The method of the present invention also relates to the introduction of the chimeric gene of the present invention into tobacco pollen. The method of the present invention also relates to the introduction of the chimeric gene of the present invention wherein the gene is β-glucuronidase. The method of the present invention further relates to the introduction of the chimeric gene into pollen and plants by microprojectile bombardment.

The invention also relates to a transformed pollen containing a DNA sequence selected from the group consisting of from:

a) about 1 to about 80 bases upstream from the 3' end of the promoter region (SEQ ID NO: 2);

b) about 1 to about 347 base-pairs upstream from the 3' end of the promoter region (SEQ ID NO: 3);

c) about 1 to about 377 base-pairs upstream from the 3' end of the promoter region (SEQ ID NO: 4);

d) about 1 to about 464 base-pairs of DNA upstream of the 3' end of the promoter region (SEQ ID NO: 5);

e) about 1 to about 595 base-pair upstream from the 3' end of the promoter region (SEQ ID NO: 6);

f) about 1 to about 1579 base-pairs of DNA upstream from the 3' end of the promoter region (SEQ ID NO: 7); and g) about 1 to about 2687 base-pairs upstream from the 3' end of the promoter region (SEQ ID NO: 8).

The invention also relates to a tobacco pollen transformed with a DNA sequence selected from the group consisting of from:

a) about 1 to about 80 bases upstream from the 3' end of the promoter region (SEQ ID NO: 2);

b) about 1 to about 347 base-pairs upstream from the 3' end of the promoter region (SEQ ID NO: 3);

c) about 1 to about 377 base-pairs upstream from the 3' end of the promoter region (SEQ ID NO: 4);

d) about 1 to about 464 base-pairs of DNA upstream of the 3' end of the promoter region (SEQ ID NO: 5);

e) about 1 to about 595 base-pair upstream from the 3' end of the promoter region (SEQ ID NO: 6);

f) about 1 to about 1579 base-pairs of DNA upstream from the 3' end of the promoter region (SEQ ID NO: 7); and g) about 1 to about 2687 base-pairs upstream from the 3' end of the promoter region (SEQ ID NO: 8).

Northern blot of RNA from various maize tissues. 2μg poly A+ RNA from 1, pollen; 2, emergent tassel; 3, emerging tassel; 4, pre-emergent tassel; 5, coleoptyle; 6, leaf; 7, root; 8, cob; and 9, silk were probed with the cDNA clone 3C12.

FIGS. 2A(1)–2C(2)

In situ hybridizations of the 3C12 cDNA to sections of maize anthers and flowers probed with antisense (1) and sense (2) probes. FIG. 2A(1) and FIG. 2A(2): Section through a maize spikelet with anthers at premeiotic stage (PM) and meiotic stage (M). FIG. 2B(1) and FIG. 2B(2): Section through a maize anther at first pollen mitosis. FIG. 2C(1) and FIG. 2C(2): Section through a maize anther just prior to dehiscence.

FIGS. 3A–3C

Nucleotide sequence of upstream 2.87 kbp of W2247 (SEQ ID NO: 1). The ATG start and putative 'TATA' box are underlined. The homologies to PB core motif and LAT 56/59 box are overlined and the transcription start is marked with an arrow. The numbers given are positions relative to the transcription start.

Homology between upstream region of maize and tobacco PG genes.

FIG. 4

Primer extension using the primer 'GTTGCCTGGGCACTAGG' on (1) Poly A+RNA from pollen, (2) Total Pollen RNA, (3) Poly A+ RNA from Cob and (4) tRNA. The sequence ladder was obtained using the same primer on W2247. The asterisk indicates the major transcription start and the dot indicates a minor product.

FIG. 5

Southern blot of genomic DNA from maize digested with NcoI and BamHI and probed with a 1.3 kbp NcoI probe from clone B7317. The copy number standards were a linearized 3.3 kbp subclone of W2247.

FIG. 6

Homologies in the upstream region of W2247 with the PB core motif and LAT 56/59 box.

FIG. 7

Translational Fusions of upstream region of W2247 to β-glucuronidase coding region.

Figure 5:
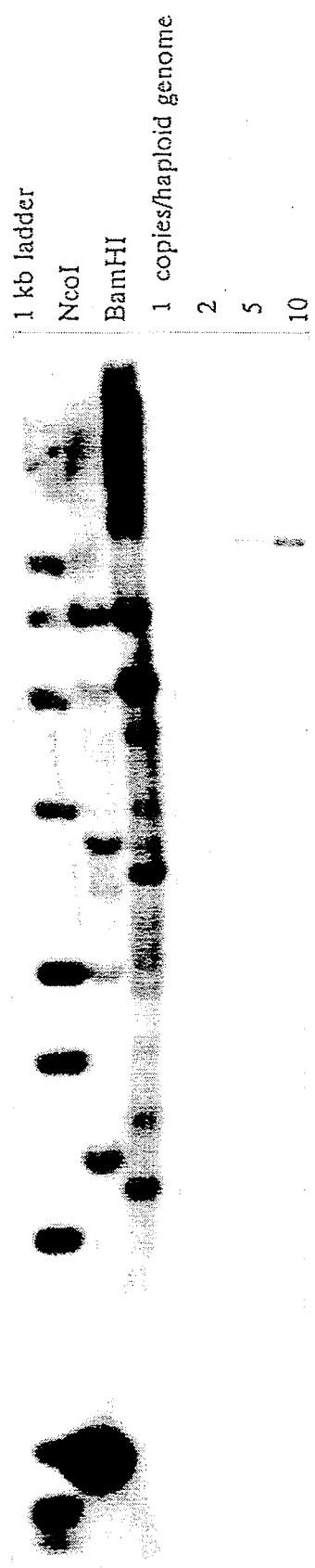

FIG. 8 5' Deletion derivatives of p47,427

FIG. 9

Relative promoter activities of the full length, p47.427 (SEQ ID NO: 8), and 5' deletion derivatives in a transient assay system. Three replicate bombardments were carried out for each plasmid tested and results are expressed as a ratio of GUS to luciferase activity. The sizes of the upstream region 5' to the transcription start are shown.

FIG. 10

Tissues of maize and tobacco were bombarded with the transcriptional and translational fusions and with the deletion derivatives. After staining with X-Gluc the activity was expressed as presence or absence of blue spots. NT, not tested.

DETAILED DESCRIPTION OF THE INVENTION

Materials and Methods

RNA Isolation and Northern Analysis

Tissues were harvested from greenhouse grown plants, rapidly frozen in liquid nitrogen and stored at −70° C. Coleoptyles and roots were obtained by germinating kernels in the dark for 4–5 days at 22° C., followed by freezing as described above. Poly A+ RNA was isolated by the method of Baulcombe and Buffard (1983). Northern transfer from formaldehyde-containing gels was carried out according to Maniatis et al. (1982) onto Genescreen plus membranes (DuPont Wilmington, Del.) and probed with a random-primed probe (Feinberg and Vogelstein, 1987) of the cDNA clone, 3C12 (Rogers et al. 1991). Filters were hybridized in a solution of 50% formamide; 5×SSC (20× SSC=3M Na₂Citrate.2H₂O, pH 7.0); 10× Denhardt's solution (Denhardt's solution=20g/l Ficoll 400, 20g/l polyvinylpyrrolidone, 10 g bovine serum albumin [Fraction V]; 100 μg/ml herring sperm DNA at 42° C. and washed in 0.1× SSC; 0.1% SDS at 65° C.

Southern Analysis

Genomic DNA was isolated by the method of Dhillon et al. (1980) and digested with restriction endonucleases, separated by electrophoresis and transferred to a nylon membrane by the alkaline transfer method of Rigaud et al. (1987). The DNA was cross-linked to the membrane by ultraviolet irradiation. The filters were probed with random primed nP-labelled DNA fragments (Feinberg and Vogelstein, 1987), hybridizing at 65° C. in a solution of 5× SSC, 5× Denhardt's solution, 0.1% SDS and 100 μg/ml sheared and denatured herring sperm DNA. Washes were performed at 65° C. in 0.1× SSC, 0.1% SDS and the filters were subjected to autoradiography at −70° C.

Sequencing

Sequencing was carried out by the dideoxy chain termination method of Sanger et al., (1977), adapted for double stranded templates by Murphy and Kavanagh (1988). A nested set of templates were generated by digestion with Exonuclease III and S1 nuclease according to the method of Henikoff (1987). The sequencing reactions were primed using the M13 primers.

Primer Extension

Primer extension of pollen RNA was carried out by standard protocols (Ausubel et al., 1987). The γ-labelled oligonucleotide was generated using polynucleotide kinase according to Maniatis et al. (1982). 4×10⁵ cpm of probe was used in the reaction. The products of the extension were analyzed by electrophoresis on a 6% polyacrylamide sequencing gel followed by autoradiography at −70° C.

In Situ Hybridization

Riboprobes used for in situ hybridization were generated from the cDNA, 3C12, cloned in pUBS3. pUBS3 was prepared by removing a DraI site from pUC18 by digestion with AatII and NdeI, followed by blunting with T4 polymerase, ligation of the blunt ends and transformation. The resulting plasmid was digested with PvuII to remove the polylinker fragment and the corresponding PvuII fragment from the Stratagene vector Bluescript® KS (Stratagene, La Jolla Calif.) was inserted (Murphy et al., 1992).

The plasmid pUBS3 containing the 3C12 cDNA was linearised and 1 μg in vitro transcribed using T3 and T7 polymerases in a reaction containing 4 mM Tris HCl; 8 mM MgCl₂; 2 mM spermidine; 50 mM NaCl; 1 mM ATP, GTP and CTP; 0.65 mM UTP; 0.35 mM DIG-UTP (Boehringer Mannheim Cat No. 1209 256); 25u RNase inhibitor to produce both sense and antisense probes respectively. Both digoxigenin(DIG)-labelled and ³⁵S-labelled probes were employed. Tissues were fixed in formaldehyde, embedded in paraffin wax, sectioned at 15 μm thickness and hybridised as described by Jackson (1991). Sections labelled with radioactive probes were exposed to emulsion for two weeks. Detection of the DIG-labelled probes was carried out using the Boehringer Mannheim Nucleic Acid Detection Kit (Cat No. 1 1175 041) with the following modifications: 100 μl of a 1:3000 dilution of <DIG> Alkaline phosphatase(AP)-conjugate were added per slide and incubated overnight at 4° C. The color detection reaction was carried out for 4–5 hours, before stopping with TE (10 mM Tris HCl pH7.5; 1 mM EDTA) .

Microprojectile Bombardment

The method of Twell et al. (1989) was employed for the bombardment of tobacco pollen grains. The plasmid DNA was adsorbed onto tungsten microprojectiles in the presence of spermidine as described by Lonsdale et al. (1990). The reporter genes used in this assay were E. coli β-glucuronidase (GUS) or firefly luciferase. 10 mg of pollen was bombarded per plate. The bombarded plates were incubated overnight at 25° C. in the light before assaying for β-glucuronidase and luciferase activities. GUS activity was determined using a fluorometric assay according to the method of Jefferson (1987). Luciferase activity was assayed according to Ow et al. (1986) and was measured on a Berthold luminometer. For the bombardment of whole tissues, the tissue was placed in MS medium supplemented with sucrose and 1% agar on a piece of Whatman no. 1 and bombarded with the deletion derivative alone. The plates were incubated at 25° C. in the light for 2 days then the tissue was transferred to a solution of 5-Bromo-4-chloro-3-indolyl-beta-D-glucuronic acid (X-Gluc) (1 mg/ml); 50 mM sodium phosphate pH 7.0; 0.1 mM Ferricyanide; 0.1% Triton X-100 and incubated for 6 hours at 37° C. For pollen samples, the nylon membrane was transferred to a piece of Whatman no. 1 filter paper soaked in the X-Gluc solution and incubated as described above. Tissues expressing GUS stain blue in this system.

Spatial Specificity of Polygalacturonase Expression

Figure 1:
FIG. 1

The polygalacturonase 3C12 cDNA described above was used to probe Northern blots containing maize poly A+ mRNA isolated from anthers, tassels at different stages of maturity, pollen, silks, cobs, leaves, roots and coleoptyles. A transcript of approximately 1.5 kbp was detected in all the anther mRNA preparations and in mature pollen (FIG. 1). The transcript was present at low levels in immature anthers increasing to a maximum in mature pollen. No hybridization was seen to any of the mRNA isolated from vegetative tissue samples.

In order to determine the cellular specificity of the transcript within the anther, in situ hybridizations were carried out using both sense and antisense riboprobes that were synthesized from the 3C12 cDNA and labelled with digoxigenin-UTP. Consistent with the results of the Northern hybridization, no hybridization of either the sense or the antisense probe was detected in the cob, leaf, silk or root sections. Sections of anthers at different developmental stages, as judged by anther color, ratio of anther length to glume length and tassel position on the plant (Chang and Neuffer 1989), were also probed with the sense and antisense probes. Each maize floret within a spikelet contains 2 sets of 3 anthers and the 2 sets are at different developmental stages. A transverse section through a floret which contained 3 premeiotic anthers and 3 meiotic anthers showed no hybridization to the sense or antisense probes (FIG. 2A). However, a transverse section through an anther at first pollen mitosis showed hybridization of the antisense probe alone to the maturing microspores (FIG. 2B). There was no hybridization to the anther wall or tapetal cell layer. A transverse section through an anther containing mature pollen just prior to dehiscence showed the same pattern of hybridization as that at first pollen mitosis (FIG. 2C). The use of $^{35}$S-labelled riboprobes also showed that expression was localized to the pollen grain and not in any of the sporophytic tissues tested. These data firmly establish that the expression of this particular polygalacturonase gene is pollen-specific.

Isolation of PG Genomic Clones

Four genomic clones were isolated from libraries of maize made in EMBL3 (Allen and Lonsdale, submitted for publication). Two of the clones, that were isolated from a library of variety B73, B7317 and B7339 were full length. The other two, that were isolated from a library of variety W22, W2247 and W2265 were incomplete at their 3' ends. DNA sequence analysis revealed that these four clones were highly homologous in their coding sequences (>99%) and appear to be members of a gene family. The full length clones do not contain introns. The nucleotide sequence of 2.87 kbp of DNA upstream from the predicted ATG start of clone W2247 has been determined (FIGS. 3A–3C). Limited sequencing of the other 3 clones indicate that the upstream regions of the 4 clones are as highly homologous in their nucleotide sequence as are their coding regions.

Mapping of the Transcription Start Site of Clone W2247

Figure 4:
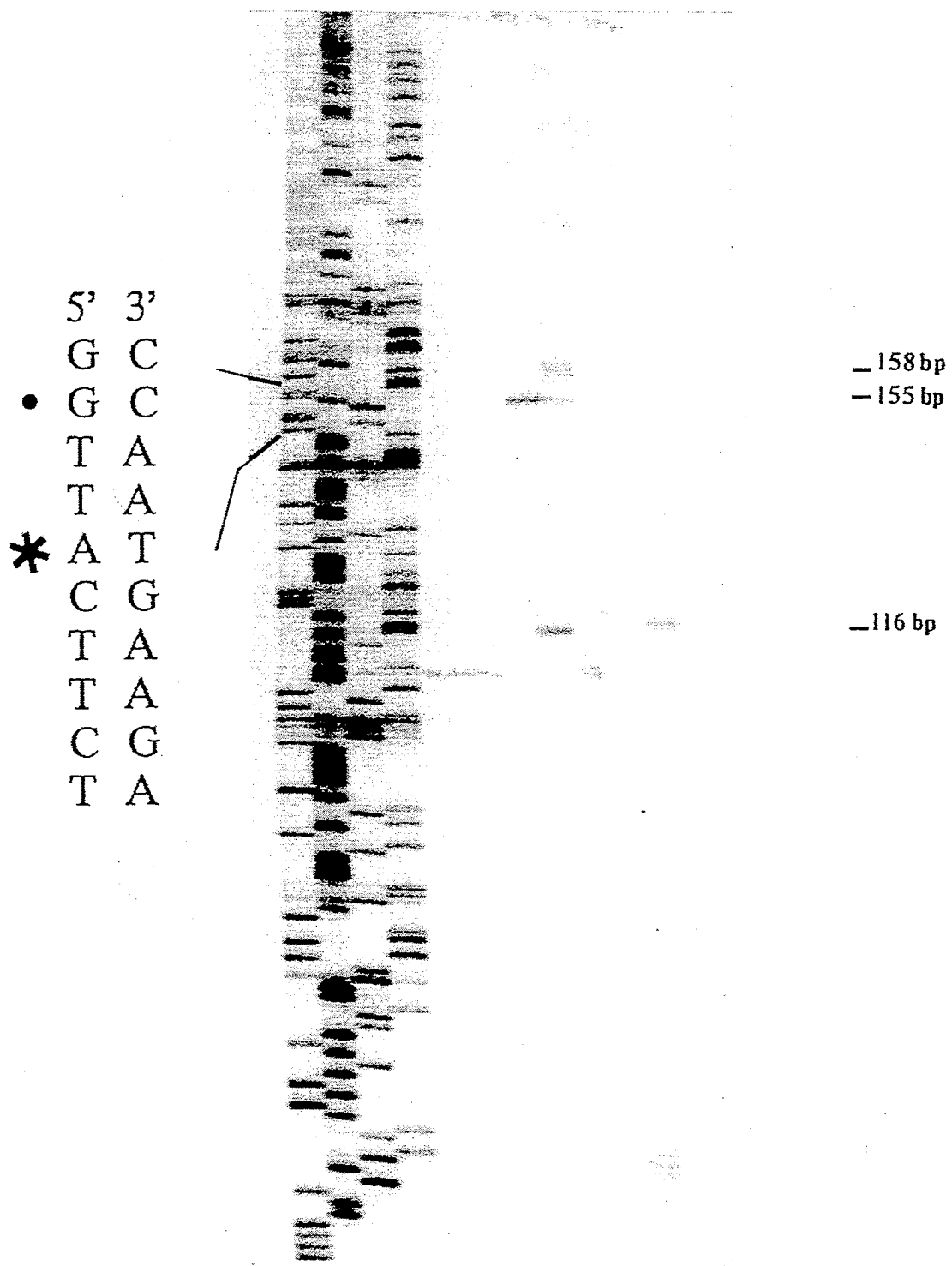

The transcription start site of clone W2247 (SEQ ID NO: 1) has been mapped by primer extension of pollen RNA. A primer (GTTGCCTGGGCACTAGG) at −53 bp relative to the putative translation initiation codon was annealed to poly A+ RNA and extended as described in Materials and Methods and a major product of 155 bp obtained (FIG. 4). A minor product of 158 bp was also obtained suggesting that either the gene has 2 transcription initiation points, or the minor product represents transcriptional initiation from other members of the gene family. Primer extensions using total RNA as substrate instead of poly A+ RNA yielded products of 155 bp, 158 bp and several larger products. These may be due to hybridization of the oligonucleotide to other unrelated non-poly A+ transcripts. In addition, a product of 116 bp was generated. This latter product probably represents an artifact because it was also synthesized when tRNA was employed as substrate. The 155 bp product established that the initiation of transcription was from the 'A' residue at 188 bp relative to the predicted ATG translational start. A putative TATA motif, 'TATTTAA' is located at −35 bp to this transcription start. An identical sequence has been found in the Zm13 pollen-specific gene of maize at −34 bp to the transcription start (Hamilton et al. 1989).

Gene Copy Number

The copy number of the polygalacturonase gene was determined by Southern blot analysis as described in Materials and Methods. Total genomic DNA from maize B73 was digested with NcoI and BamHI, separated by electrophoresis, blotted to a nylon membrane and probed with a 1.3 kbp NcoI fragment of clone B7317. This probe hybridized to multiple bands (FIG. 5). Comparison of these bands with gene copy number standards suggest that they were present in more than five copies per cell indicating that the gene is probably a member of a gene family. The fainter hybridizing bands may represent members of the PG gene family which are not pollen-specific and exhibit less homology to the pollen-specific clone used as a probe. The suggestion that the pollen-specific maize PG gene is a member of a multigene family is in agreement with the results obtained with the pollen-specific PG cDNA clone of O. organensis (Brown and Crouch 1990) and also with our results obtained from a comparison of restriction maps and nucleotide sequence of 3 genomic clones of the maize PG (Allen and Lonsdale submitted for publication).

Sequence Analaysis

The 2.87 kbp of upstream sequence of clone W2247 (SEQ ID NO: 1) was sequenced by the methods described in Materials and Methods and analyzed for homologies with potential cis-acting sequences identified in other anther and pollen-specific genes. The sequence is shown in FIGS. 3A–3C (SEQ ID NO: 1). An analysis of the upstream regions of three pollen-expressed genes from tomato (Twell et al. 1991) revealed two cis-acting sequences important for expression in pollen. These were 'TGTGGTT', termed the PB core motif and 'GAAPuTTGTGA', the LAT 56/59 box. The motifs 'GTGG' and 'GTGA', the mutation of which lead to decreased activity of the promoters, are also present in the upstream regions of Zm13 and the petunia CHIA-P$_{A2}$ gene (van Tunen et al. 1989). In the 2.87 kbp of upstream region of the maize PG gene, we found seven sequences with at least 5/7 matches to the PB core motif including the 'GTGG' motif (FIG. 6). Six sequences with at least 7/10 matches to the LAT 56/59 box including the 'GTGA' motif were also found.

The proposed ATG start has 67% homology to the consensus plant translation initiation region proposed by Lutcke (1987) and is predicted to be the correct ATG start as it is the first in frame methionine codon.

A comparison of the upstream region of clone W2247 (SEQ ID NO: 1) with that of Zm13 revealed some homologies, but these were at varying distances from the transcription starts in the two genes. There is a series of direct repeats in the upstream region of clone W2247 (SEQ ID NO: 1), which are similar to structures present in the upstream sequence of Zm13. The function, if any, of these structures is as yet unknown. The only significant homology between them was an identical putative TATA box 'TATTTAA'. This lack of homology in the upstream regions of genes from the same species expressed in the same tissue in a tissue-specific manner has also been reported for other sets of genes (McCormick 1991). Some sequence homologies were found to the motifs identified by Hamilton et al. (1989) in the upstream regions of some anther and pollen-expressed genes. However, there is no evidence for these sequences being involved in expression. There are no striking homologies between the upstream region of clone W2247 and the conserved sequences in the upstream regions of two pollen-specific genes from *Brassica napus* (Albani et al. 1991).

The tobacco gene for polygalacturonase (PG) has been cloned and sequenced (Tebbutt and Lonsdale, unpublished). A comparison of the nucleotide sequences of the tobacco and maize PG's upstream of the coding region reveals little homology except for one region. This sequence is not present in the upstream region of any other pollen-specific gene published and therefore does not appear to be an absolute requirement for pollen-specific expression. It occurs at similar positions relative to the respective transcriptional starts, at −117 bp in maize and −140 bp in tobacco. The conserved 9 bp within this sequence is also present in the upstream region of the PG involved in fruit-ripening in tomato at −700 bp. The involvement of this sequence in the pollen-specific expression of the maize and tobacco PG genes is under investigation.

DESCRIPTION OF THE PREFERRED EMBODIMENTS

Promoter Activity of Clone W2247 and Deletion Derivatives

Figure 7:

The entire upstream region of clone W2247 (SEQ ID NO: 1) was fused to the coding region of the Escherichia coli β-glucuronidase (GUS) gene to generate chimeric genes for the assay of effective gene expression by this maize promoter (FIG. 7). A translational fusion, p47.427 (SEQ ID NO: 8) was created by the fusion of a blunted ApaLI fragment of a 2.75 kbp from clone W2247 to a blunted BamHI site of pTAK1 (Jefferson et al., 1987), a pUC-based vector containing a promoterless GUS gene and the nos terminator sequence. p47.427 (SEQ ID NO: 8) was thus fused at +10 bp to the native ATG and contained 3 codons from clone W2247 and 8 codons from the vector preceding the ATG of the GUS coding region. A reverse translational fusion, p47.430, was created by the fusion of the SmaI/SalI fragment of p47.427 containing the entire upstream region blunted and inserted in the opposite orientation in pTAK1 cut with SmaI and SalI and blunted.

In order to delimit the areas of the upstream region responsible for the pollen-specific expression, a nested set of deletion derivatives of p47,427 (SEQ ID NO: 8) were generated from the 5' end of the insert (FIG. 8) according to the method of Henikoff (1989). Deletion derivatives were assayed for promoter activity using a transient assay system based on the microprojectile bombardment of tobacco pollen (Twell et al. 1990) as described in Materials and Methods. Tobacco transformation experiments had revealed that the 2,687 kbp of upstream region of clone W2247 could activate expression of the GUS gene in a manner analogous to its activity in the native background (Allen and Lonsdale, unpublished). Tobacco pollen was co-bombarded with the deletion molecules and a reference plasmid. The reference plasmid was used to standardize between bombardments and consisted of the upstream region of a pollen-expressed actin gene fused to the firefly luciferase coding region and the nos terminator. Activity was measured as the relative activity of GUS to luciferase in each bombardment. Three replicate bombardments were performed for each of the plasmids tested.

Figure 9:
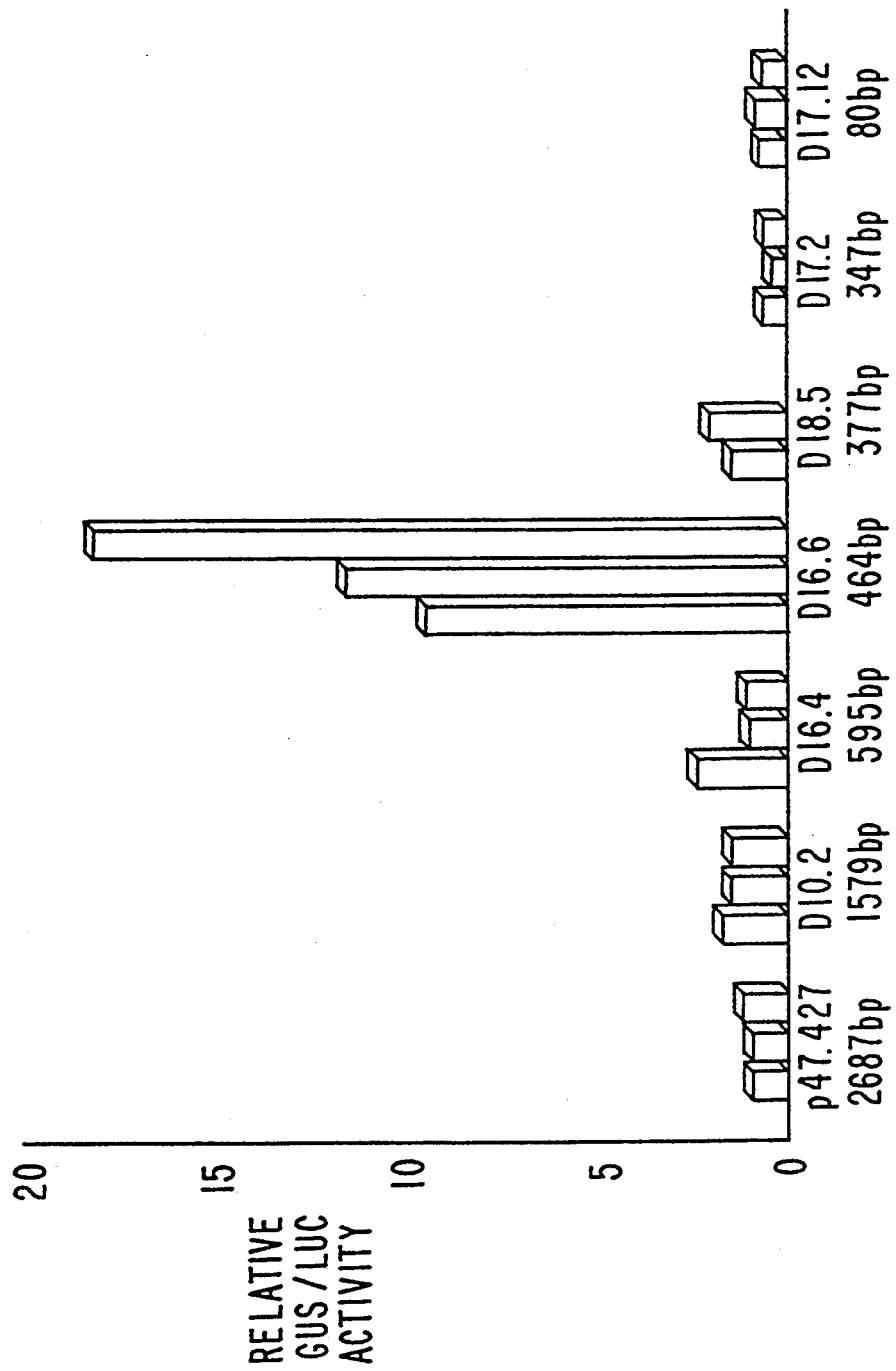

FIG. 8 shows preferred embodiments of the present invention in graphic form. The deletion derivative D16.6 (SEQ ID NO: 5) represents a more preferred embodiment of the present invention. FIG. 9 shows the activities of the deletion derivatives when assayed in the transient expression system described above. All of the deletion derivatives exhibited similar activities with respect to the full length sequence p47.427 (SEQ ID NO: 8). However, the more preferred embodiment D16.6 (SEQ ID NO: 5) which contained 464 bp of upstream region, exhibited 9 to 18 times the expression level of the full length clone p47,427 (SEQ ID NO: 8). The deletion derivatives were also tested to determine whether they retained pollen-specificity by microprojectile bombardment of a variety of maize and tobacco tissues, followed by staining with X-Gluc. The presence of blue spots indicates expression of the deletion derivatives. The CaMV (cauliflower mosaic virus) 35S promoter fused to the maize Adh1 intron and the GUS coding region (CAMV ADH::GUS) was used as a positive control for expression. This was shown to be active in all maize and tobacco tissues tested. In these experiments, the deletion derivatives maintained their tissue-specificity since they exhibited GUS activity only in tobacco pollen and not in tobacco leaf or any other maize tissue tested (FIG. 10). Deletion derivative D17.12 (SEQ ID NO: 2), which contained only 80 bp of sequence upstream of the transcriptional start, exhibited some weak expression. This was comparable with that exhibited by the CAMVADH::GUS construction and the p47.430.

Reports of the tissue-specificity of maize monocotyledonous promoters being faithfully conserved in transgenic dicotyledonous plants (Guerrero et al. 1990) suggest a sequence conservation of the binding sites for the putative transacting factors involved. Other investigators have identified so called "pollen boxes" which, in one case, have been shown to affect expression in pollen. Motifs similar to the PB core motif identified by Twell et al. (1991) in the upstream region of the LAT genes have been found in the upstream region of W2247, however all of these, except for that at −8 to −14, occur at least 1kb upstream of the transcriptional start, a region not required for pollen-specific expression.

In the LAT52 gene the minimal promoter required for pollen expression is from −71 to +110 (Twell et al. 1991). We have shown that in a tobacco semi-in vivo system that the region −80 to +5 exhibits weak pollen-specific expression. Within the 87 bp between the 5' end of D16.6 (SEQ ID NO: 5) and D18.5 (SEQ ID NO: 4) there appears to be a region which promotes expression from the maize PG promoter in tobacco pollen to a much enhanced level compared with the full length clone. This activity is substantially reduced by the presence of further upstream sequences. See FIG. 9.

Introduction of Pollen-Specific Chimeric Genes into Plants, Plant Cells and/or Plant Protoplasts Having defined the pollen-specific PG promoter of the present invention, and demonstrated the ability of the isolated sequences to drive the expression of an exogenous gene (β-glucuronidase) in tobacco pollen it is now possible to use these sequences to facilitate the introduction and expression of chimeric genes in plants and in pollen.

On this basis, the present invention also relates to a chimeric gene and transfer vector consisting essentially of the PG promoter region set forth FIGS. 3A–3C or any one of the deletion derivatives of FIGS. 8 and 9 and a exogenous gene (lacking it's wild-type promoter) whose expression may be regulated by any of the sequences described above.

Techniques for the introduction of vectors into plants or plant cells are well known in the art. Such methods include but are not limited to calcium phosphate-coprecipitation techniques, protoplast fusion, electroporation, microprojectile mediated transfer, infection with viruses, and infection with bacteria (e.g., *Agrobacterium tumifaciens*) (Jones, 1985).

An example of how a pollen-specific chimera can be used in this context is described above wherein an *E. coli* β-glucuronidase gene was successfully transferred into and expressed in tobacco pollen and tobacco leaf tissue.

By way of another example, the bacteria *Agrobacterium tumifaciens* may be used to introduce the chimeric genes of the present invention into plants, plant cells or protoplasts. More specifically, the promoter sequences of the present invention may be ligated to a reporter gene such as β-glucuronidase as described above and further incorporated into a Ti plasmid such as pBI101.2 and introduced into *Agrobacterium tumifaciens* by standard procedures. (Horsh et al. 1985). This bacterium may then be used to introduce the plasmid into plants by techniques well known in the art. (Horsh et al. 1985)

The method of the present invention may be used to introduce genes into pollen for the purpose of arresting pollen development thereby rendering a plant male sterile. Such genes may include those coding for proteins toxic to pollen. It is also contemplated that chimeric plasmids may be constructed which allow the expression of antisense mRNAs which are capable of inhibiting expression of genes which play a role in pollen development.

It is also contemplated that the vectors of the present invention may be useful for the introduction of useful phenotypic characteristics into pollen which may include but are not limited to pesticide resistance, resistance to or toxicity to insect pests, or which optimize other pollen functions.

REFERENCES

Albani, D., Altosaar, I., Arnison, P. G. and Fabijanski, S. F. (1991). A gene showing sequence similarity to pectin esterase is specifically expressed in developing pollen of *Brassica napus*. Sequences in its 5' flanking region are conserved in other pollen-specific promoters. Plant. Mol. Biol. 16;501–513.

Allen R. L and Lonsdale D. M. Sequence analysis of three members of the maize polygalacturonase gene family expressed during pollen development. (Submitted for publication).

Ausubel, F. M., Brent, R., Kingston, R. E., Moore, D. D., Seidman, J. G., Smith, J. A. and Struhl, K. (Eds.) (1987). Current Protocols in Molecular Biology. John Wiley and Sons, New York.

Baulcombe, D. C. and Buffard, D. (1983). Gibberellic acid-regulated expression of α-amylases and six other genes in wheat aleurone layers. Planta 157;493–500.

Brown S. M. and Crouch M. L. (1990). Characterization of a gene family abundantly expressed in *Oenothera organensis* pollen that shows sequence similarity to polygalacturonase. The Plant Cell 2;263–274.

Chang M. T. and Neuffer M. G. (1989). Maize microsporogenesis. Genome 32;232–244.

Dhillon S. S., Rake A-V. and Miksche J. P. (1980). Reassociation kinetics and cytophotometric characterization of peanut (*Arachis hypogaea* L.) Plant Physiol. 65;1121–1127.

Feinberg, P. and Vogelstein, B. A technique for radiolabelling DNA restriction endonuclease fragments to high specific activity. Anal. Biochem. 132:6–13, 1987.

Grierson, D., Tucker G. A., Keen J., Ray J., Bird C. R. and Schuch W. (1986). Sequencing and identification of a cDNA clone for tomato polygalacturonase. Nucl. Acids Res. 14;8595–8603.

Guerrero F. D., Crossland L., Smutzer G. S., Hamilton D. A. and Mascarenhas J. P. (1990). Promoter sequences from a maize pollen-specific gene directs tissue specific transcription in tobacco. Mol. Gen. Genet. 224;161–168.

Hamilton D. A., Bashe D. M., Stinson J. R. and Mascarenhas J. P. (1989). Characterization of a pollen-specific genomic clone from maize. Sex Plant. Reprod. 2;208–212.

Hanson, D. D., Hamilton, D. A., Travis, J. L., Bashe, D. M. and Mascarenhas, J. P. (1989). Characterization of a pollen-specific cDNA clone from Zea mays and its expression. Plant Cell 1;173–179.

Henikoff S. (1987). Unidirectional digestion with exonuclease III in DNA sequence analysis. Meth. Enz. 155;156–165.

Horsh, R. B., Frey, J. E., Hoffman, N. L., Eicholtz, D., Rogers, G., and Fraley, R. T. (1985). A Simple and General Method for Transferring Genes Into Plants. Science 277;1229–1231.

Jackson, D. P. (1991). In situ hybridization in plants. In: Molecular Plant Pathology: A Practical Approach. D. J. Bowles, S. J. Gurr and M. McPhereson (Eds) Oxford University Press, Oxford.

Jefferson, R. A., Kavanagh, T. A. and Bevan, M. W. (1987). GUS fusions: β-glucuronidase as a sensitive and versatile gene fusion marker in higher plants. EMBO J. 3901–3907.

Jones, M. G. K. (1985). Transformation of Cereal Crops by Direct Gene Transfer. Nature 37;579–580.

Lonsdale, D. M., Onde, S. and Cuming, A. (1990). Transient expression of endogenous DNA in intact viable wheat embryos following particle bombardment. J. Exp. Bot. 41;1161-1165.

Lutcke, H. A., Chow, K. L., Mickel, F. S., Moss, K. A., Kem, H. F. and Scheele, G. A. (1987). Selection of AUG initiation codons differs in plants and animals. EMBO J. 6;43-48.

McCormick S. (1991). Molecular analysis of male gametogenesis in plants. Trends in Genetics 7;298-303.

Maniatis, T., Fritsch, E. F. and Sambrook, J. (1982). Molecular Cloning: a laboratory manual. Cold Spring Harbor Laboratory Press, Cold Spring Harbor, New York.

Mascarenhas, J. P. (1990). Gene activity during pollen development. Ann. Rev. Plant Physiol. Plant Mol. Biol. 41;317-338.

Murphy, G. and Kavanagh, T.A. (1988). Speeding up the sequencing of double-stranded DNA. Nucl. Acids. Res. 16;5198.

Murphy, G. J. P., Lucas, G., Moore, G., and Flavell, R. B. (1992). Sequence Analysis of Wis-2-1A, a Retroposon-Like Element from Wheat. Plant Mol. Biol., in press.

Ow, D. W., Wood, K. V., DeLuca, M., DeWet, J. R., Helinski, D. R. and Howell, S. H. (1986). Transient and stable expression of the firefly luciferase gene in plant cells and transgenic plants. Science 234;856-859.

Pressey, R. and Reger, B. J. (1989). Polygalacturonase in pollen from corn and other grasses. Plant Science 59;57-62.

Rigaud, G. F., Grange, T. and Pictet, R. (1987). The use of NAOH as transfer solution of DNA onto nylon membrane decreases the hybridization efficiency. Nucl. Acids. Res. 15;857.

Rogers, H. J., Allen, R. L., Hamilton, W. D. O. and Lonsdale, D. M. (1991). Pollen-specific cDNA clones from Zea mays. Biochem. Biophys. Acta. 1089;411-413.

Sanger, F., Nicklen, S. and Coulson, A. R. (1977). DNA sequencing with chain terminating inhibitors. Proc. Natl. Acad. Sci. USA 74;5463-5467.

Stinson, J. R., Eisenberg, A. J., Willing, R. P., Pe, M. E., Hanson, D. D. and Mascarenhas, J. P. (1987). Genes expressed in the male gametophyte and their isolation. Plant Physiol. 83;442-447.

van Tunen, A. J., Hartman, S. A., Mur, L. A. and Mol, J. N. M. (1989). Regulation of chalcone flavanone isomerase (CFI) gene expression in Petunia hybrids: the use of alternative promoters in corolla, anthers and pollen. Plant Mol. Biol. 12;539-551.

Twell, D., Klein, T. M., Fromm, M. E. and McCormick, S. (1989). Transient expression of chimeric genes delivered into pollen by microprojectile bombardment. Plant Physiol. 91;1270-1274.

Twell, D., Yamaguchi, J., Wing, R. A., Ushiba, J and McCormick, S. (1991). Promoter analysis of 3 genes that are coordinately expressed during pollen development reveals pollen-specific enhancer sequences and shared regulatory elements. Genes Dev. 5;496-507.

Willing, R. P., Bashe, D. and Mascarenhas, J. P. (1988). An analysis of the quantity and diversity of mRNAs from pollen and shoots of Zea mays. Theor. Appl. Genet. 75;751-753.

---

We claim:

1. An isolated and purified DNA molecule consisting essentially of a nucleotide sequence which is selected from the group consisting of SEQ ID NO: 2, SEQ ID NO: 3, SEQ ID NO: 4, SEQ ID NO: 5, SEQ ID NO: 6, SEQ ID NO: 7 and SEQ ID NO: 8.

2. An isolated and purified DNA molecule consisting essentially of the nucleotide sequence of SEQ ID NO: 5.

3. A pollen-specific chimeric gene comprising:
   (a) the DNA molecule as in either claim 1 (SEQ ID NO: 2-8) or claim 2 (SEQ ID NO: 5); and
   (b) an exogenous gene,
wherein said DNA molecule regulates the expression of said exogenous gene in a pollen-specific manner.

4. A transfer vector comprising the pollen-specific chimeric gene of claim 3.

5. An isolated and purified DNA molecule that consists of a nucleotide sequence which is selected from the group consisting of SEQ ID NO: 2, SEQ ID NO: 3, SEQ ID NO: 4, SEQ ID NO: 5, SEQ ID NO: 6, SEQ ID NO: 7 and SEQ ID NO: 8.

6. An isolated and purified DNA molecule consisting of the nucleotide sequence of SEQ ID NO: 5.

7. A pollen-specific chimeric gene comprising:
   (a) the DNA molecule of claim 5; and
   (b) an exogenous gene,
wherein said DNA molecule regulates the expression of said exogenous gene in a pollen-specific manner.

8. A transfer vector comprising the pollen-specific chimeric gene of claim 7.

9. A pollen-specific chimeric gene comprising:
   (a) the DNA molecule of claim 6 (SEQ ID NO: 5); and
   (b) an exogenous gene,
wherein said DNA molecule regulates the expression of said exogenous gene in a pollen-specific manner.

10. A transfer vector comprising the pollen-specific chimeric gene of claim 9.

* * * * *